United States Patent [19]

McCarroll et al.

[11] 4,055,628

[45] Oct. 25, 1977

[54] METHOD FOR PREPARING GRAPHITE CONTAINING CARBON

[75] Inventors: John James McCarroll, Camberley; John Trevor Kent Clark, Weybridge; Stephen Robert Tennison, New Haw, all of England

[73] Assignee: The British Petroleum Company Limited, London, England

[21] Appl. No.: 725,586

[22] Filed: Sept. 22, 1976

Related U.S. Application Data

[63] Continuation-in-part of Ser. No. 606,420, Aug. 21, 1975, abandoned.

[30] Foreign Application Priority Data

Sept. 2, 1974 United Kingdom ............... 38182/74
Sept. 2, 1974 United Kingdom ............... 38183/74

[51] Int. Cl.² .................. C01B 31/02; C01B 31/04; B01J 21/18
[52] U.S. Cl. .................. 423/448; 252/445; 252/447; 423/460; 423/445
[58] Field of Search ............... 423/448, 449, 460, 461, 423/445; 252/444, 445, 447, 421; 106/307

[56] References Cited

U.S. PATENT DOCUMENTS

| | | | |
|---|---|---|---|
| 1,780,154 | 11/1930 | Gardner | 423/445 X |
| 2,479,708 | 8/1949 | Amon | 423/460 |
| 2,516,233 | 7/1950 | McKinnis | 252/421 |
| 2,683,652 | 7/1954 | Martin | 423/461 |

OTHER PUBLICATIONS

Dannenberg et al., "Industrial and Engineering Chemistry", vol. 47, No. 2, 1955, pp. 339–344.
Kirk–Othmer Encyclopedia of Chemical Technology, vol. 4, 1964, pp. 248–249.
Atkins, "Carbon" 1965, vol. 3, pp. 299–303.

*Primary Examiner*—Edward J. Meros
*Attorney, Agent, or Firm*—Morgan, Finnegan, Pine, Foley & Lee

[57] ABSTRACT

Graphite-containing carbon is prepared by subjecting carbon to the steps of (1) an initial heat treatment in an inert atmosphere, (2) an oxidation stage and (3) a further heat treatment in an inert atmosphere.

8 Claims, No Drawings

METHOD FOR PREPARING GRAPHITE CONTAINING CARBON

This application is a continuation-in-part of application Ser. No. 606,420 filed Aug. 21, 1975, now abandoned.

This invention relates to a novel method for preparing graphite-containing carbon, especially suitable for use as a catalyst support.

According to the present invention there is provided a method for preparing graphite-containing carbon having (1) a basal plane surface area of at least 100 m$^2$/g, (2) a ratio of BET surface area to basal plane surface area of not more than 5:1 and (3) a ratio of basal plane surface area to edge surface area of at least 5:1, which method comprises the steps of (1) an initial heat treatment in an inert atmosphere at a temperature between 900° and 3300° C, (2) an oxidation stage at a temperature between 300° and 1200° C and (3) a further heat treatment in an inert atmosphere at a temperature between 1000° and 3000° C, preferably 2000° C.

Preferably the carbon initially has a BET surface area in the range 100 to 3000 m$^2$/g.

In Steps (1) and (3) nitrogen provides a suitable atmosphere for temperatures up to 1000° C. Above this, an inert gas, e.g., argon or helium, should preferably be used. In Step (2) suitable oxidising media include air, steam and carbon dioxide. If air is employed, the temperature is preferably in the range 300° to 450° C; if steam or carbon dioxide, in the range 800°–1200° C.

During the heating in the inert atmosphere a portion at least of the carbon is converted to graphite, and it is believed that adsorbed organic oxygen-containing groups such as ketones, hydroxyl, carboxylic acids and the like are removed. The absence of organic oxygen containing groups from the tested carbon (less than 1%) is believed to be significant in the context of selectivity of the catalyst employing the carbon as a support, since oxygen-containing groups have been reported to promote side reactions.

The graphite containing carbon comprises a crystalline layered structure in which the constituent atoms form layers attached to each other by relatively weak Van der Waals dispersion forces. The crystalline surface area of the material is formed largely of the basal planes of the layers with a smaller contribution from the edges of the layers. There will usually be some amorphous carbon associated with the crystalline material.

The basal surface area is determined by measuring the heat of adsorption of n-dotriacontane from n-heptane. Similarly the edge surface area is determined by the heat of adsorption of n-butanol from n-heptane.

Heats of adsorption can be measured using a flow microcalorimeter as described in "Chemistry and Industry" for Mar. 20, 1965 at pages 482–485.

The BET surface area is the surface area determined by the nitrogen adsorption method of Brunauer, Emmet and Teller disclosed in J. Am. Chem. Soc. 60, 309, (1938). This corresponds to the total surface area, i.e., the crystalline basal plane surface area, the crystalline edge surface area and the amorphous surface area.

Preferably the basal plane surface area is at least 150 m$^2$/g. If the basal plane area is greater than 1000 m$^2$/g, it is unlikely to have sufficient strength for a catalyst support.

The closer that the ratio of the BET surface area to the basal plane area is to the theoretical minimum of 1, the higher is the quality of the material, i.e., the higher is the proportion of crystalline material and the lower is the proportion of amorphous.

Preferably the ratio of the basal plane surface area to the edge surface area is greater than 10:1, most preferably greater than 300:1.

Preferably the graphite containing carbon has a pH in the range from 5 to 9, more preferably from 6 to 8, most preferably about 7, and contains less than 1% by wt. of adsorbed oxygen, more preferably less than 0.5% by wt. of adsorbed oxygen. The lower the proportion of adsorbed oxygen, the closer is the pH to 7.

Preferably the total metals content of the graphite containing carbon is less than 250 ppm. Preferably the graphite containing carbon contains less than 200 ppm, more preferably less than 100 ppm of alkali and alkaline earth metals.

The particle size of the graphite containing carbon is not significant and can be controlled in known manner in view of its intended application, ranging from fine particles for use in slurry processes to granules for use in fixed bed processes.

The graphite may be prepared from many different forms of carbon, including (a) activated carbons derived from coconut charcoal, coal, peat, etc. (b) carbons produced by the coking of petroleum residues, and (c) oleophilic graphite, e.g., as prepared according to our British Patent Specification No. 1168785.

Preferably the carbon employed as a starting material is one which, prior to heat treatment as above, at approximately 1000° C, has a BET surface area of at least 500 m$^2$/g.

The preparation of the graphite containing carbon varies according to the type of carbon selected and utilises combinations of heat treatment under inert and oxidising conditions chosen so as to optimise the ratios of BET to basal plane areas and basal plane to edge surface areas.

Heating in an inert atmosphere increases the proportion of graphitic material, i.e., decreases the first ratio and increases the second. With most forms of carbon, however, the total surface area is significantly reduced by this treatment, but this is not always the case and some forms of carbon show only a relatively small decrease in surface area on heating.

Oxidation under carefully controlled conditions, by contrast, increases the surface area.

The graphite containing carbon as defined above can be employed as a catalyst support for a large number of metals or metal-containing compound catalysts for a wide range of reactions. Because the carbon is very inert the metal or metal containing catalyst exhibits the catalytic properties of the metal.

The invention is illustrated with reference to the following Example.

EXAMPLE 1

Activated carbon AC40, supplied by CECA Ltd., was heat-treated to 900° C in nitrogen (to remove undesirable aromatic residues) and the heat treatment continued to 1500° C in argon. The resultant carbon was then, in a second step, oxidised in air at 425° C to 23 percent weight loss. This oxidised carbon was then, in the third step, reheat-treated to 1900° C and 1700° C in argon. The resultant carbons at each stage were then ground to 16–30 mesh BSS and impregnated with 1.0 percent weight Pt using a dilute solution of $H_2Pt\,Cl_6$. The catalyst was reduced in flowing hydrogen and then used to dehydrocyclise n-hexane at 500° C, 2 LHSV of n-C$_6$,10:1 H$_2$:HC, at 1 atmos total pressure.

The surface areas of the carbons produced at the various stages were: As received N$_2$ BET area m$^2$/g 1260

|  | 1st Step (to 1500° C) | 2nd Step (burn-out in air) | 3rd Step (reheat-treated to 1900° C) | 3rd Step (to 1700° C) |
|---|---|---|---|---|
| N$_2$ BET area m$^2$/g | 565 | 1107 | 310 | 539 |
| Basal area m$^2$/g | 278 | 476 | 202 | 312 |
| Edge area m$^2$/g | 11 | 56 | 0.4 | 2.4 |

A typical measure of the strength of the catalyst after the final stage is a mean piece crushing strength of 0.87 kg/mm.

The results of the n-hexane dehydrocyclisation tests after 60 minutes on stream were:

|  | 1st Step (to 1500° C) | 2nd Step (burn-out) | 3rd Step (to 1900° C) | 3rd Step (to 1700° C) |
|---|---|---|---|---|
| Conversion of n-C$_6$ | 30.4 | 40.0 | 59.5 | 40.2 |
| Benzene yield | 10.9 | 13.8 | 35.4 | 17.2 |
| Selectivity | 35.9 | 34.7 | 59.5 | 42.9 |

This clearly demonstrates the effects of heat treatment on production of the specific surfaces and the effect of these surfaces influencing the catalytic behaviour.

We claim:

1. A method for the preparation of a graphite-containing carbon having (1) a basal plane surface area of at least 100 m$^2$/g; (2) a ratio of BET surface area to basal plane surface area of not more than 5:1; and (3) a ratio of basal plane surface area to edge surface area of at least 5:1, which method comprises treating a high surface area carbon having a BET surface area of at least 500 m$^2$/g to the steps of (1) an initial heat treatment in an inert atmosphere at a temperature between 900° C and 3300° C; (2) oxidation stage by heating in an oxidizing atmosphere at a temperature between 300° and 1200° C; and (3) a further heat treatment in an inert atmosphere at a temperature between 1000° C and 3000° C.

2. A method according to claim 1 wherein the oxidation stage is carried out in an atmosphere of air at a temperature in the range 300°–450° C.

3. A method according to claims 1 wherein the oxidation stage is carried out in an atmosphere of steam or carbon dioxide at a temperature in the range 800°–1200° C.

4. A method according to claim 1 wherein the third stage is carried out at a temperature between 1000° and 2000° C.

5. A method according to claim 1 wherein the basal plane surface area is in the range 150 to 1000 m$^2$/g.

6. A method according to claim 1 wherein the ratio of the basal plane surface area to the edge surface area is greater than 10:1.

7. A method according to claim 1 wherein the ratio of the basal plane surface area to the edge surface area is greater than 300:1.

8. A method according to claim 1 wherein the high surface area carbon initially has a BET surface area up to 3000 m$^2$/g.

* * * * *